(12) United States Patent
Terwilliger

(10) Patent No.: US 6,328,701 B1
(45) Date of Patent: *Dec. 11, 2001

(54) BIOPSY NEEDLE AND SURGICAL INSTRUMENT

(75) Inventor: Richard A. Terwilliger, Estes Park, CO (US)

(73) Assignee: Medical Device Technologies, Inc., Gainsville, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 09/572,418

(22) Filed: May 17, 2000

Related U.S. Application Data

(62) Division of application No. 09/114,509, filed on Jul. 13, 1998, now Pat. No. 6,110,129.

(51) Int. Cl.[7] .................................................. A61B 17/32
(52) U.S. Cl. ............................................................. 600/567
(58) Field of Search .................................. 600/566, 567, 600/564; 606/170

(56) References Cited

U.S. PATENT DOCUMENTS

| | | | |
|---|---|---|---|
| 3,477,423 | * | 11/1969 | Griffith ................................. 600/567 |
| 3,629,912 | * | 12/1971 | Klopp . |
| 4,519,392 | * | 5/1985 | Lingua . |
| 4,699,154 | * | 10/1987 | Lindgren . |
| 4,716,886 | * | 1/1988 | Schulman et al. . |
| 4,890,626 | * | 1/1990 | Wang . |
| 4,953,558 | * | 9/1990 | Akerfeldt . |
| 4,958,625 | * | 9/1990 | Bates et al. . |
| 5,025,797 | * | 6/1991 | Baran . |
| 5,092,870 | * | 3/1992 | Mittermeier . |
| 5,163,947 | | 11/1992 | Kvalo et al. . |
| 5,224,470 | * | 7/1993 | Schnepp-Pesch et al. . |
| 5,249,582 | | 10/1993 | Taylor et al. . |
| 5,279,570 | | 1/1994 | Dombrowski et al. . |
| 5,284,156 | * | 2/1994 | Schramm et al. . |
| 5,316,031 | | 5/1994 | Striebel, II et al. . |
| 5,388,589 | | 2/1995 | Davis et al. . |
| 5,476,101 | * | 12/1995 | Schramm et al. . |
| 5,507,298 | * | 4/1996 | Schramm et al. . |
| 5,546,957 | * | 8/1996 | Heske . |
| 5,560,373 | * | 10/1996 | De Santis ............................. 600/566 |

* cited by examiner

*Primary Examiner*—Michael H. Thaler
(74) *Attorney, Agent, or Firm*—Mayer, Brown & Pratt

(57) ABSTRACT

The present invention includes a biopsy needle for use in a biopsy gun or as surgical instrument, capable of taking multiple samples, and a guiding needle holder for holding a biopsy needle. The biopsy needle includes an inner needle, also called a stylet, and an outer needle, also called a cannula, and a guiding needle holder. The stylet has a recess in the vicinity of its distal end which receives the tissue sample. The guiding needle holder includes an integrated spacer, and first and second connecting elements. The first connecting element holds the proximal end of the cannula and is displaceably attached along the length of the integrated spacer. The second connecting element holds the proximal end of the stylet and is fixedly attached to the distal end of the integrated spacer. The connecting elements each have an opening that facilitates insertion of the biopsy needle into a known biopsy gun in either the cocked or uncocked position. In an alternate embodiment, the guiding needle holder includes an integrated spacer that fixedly holds the stylet, and a connecting element that displaceably holds the cannula.

29 Claims, 4 Drawing Sheets

BIOPSY NEEDLE AND SURGICAL INSTRUMENT

This is a Divisional of and incorporates by reference application Ser. No. 09/114,509 filed Jul. 13, 1998, now U.S. Pat. No. 6,110,129.

FIELD OF THE INVENTION

This invention relates to an improved biopsy needle specially suited for use in a biopsy gun, or for use as a surgical instrument.

BACKGROUND OF THE INVENTION

Biopsy needles, as part of a biopsy system, are generally used in the medical field to remove tissue, cells or fluids from a body for examination. Known biopsy needles have at least one inner needle (stylet) and an outer needle (cannula). The stylet has a point to enable insertion of the needle into a body, and a recess or notch located near its distal end for receiving a tissue sample. The cannula is displaceably guided on the stylet and has sharp cutting edges. Both the stylet and cannula have a connecting element on their proximal ends to enable connection of the needle to the slides of a biopsy gun. The connecting elements in known biopsy needles generally have included either flanges that cooperate with matching contact surfaces on the slides, or recesses that engage a rib located on a slide wherein both the slide and the rib run along the length of the biopsy needle.

Some prior art biopsy needles have the disadvantage that it is sometimes difficult to insert them into the biopsy gun under sterile conditions. Some prior art biopsy guns require a certain spacing between the connecting elements on the stylet and cannula in order for the biopsy needle to be inserted into the biopsy gun. However, this task of inserting the biopsy needle into the biopsy gun while the connecting elements are maintained in a fixed orientation is difficult because the stylet is generally freely displaceable in the cannula. Therefore, it is generally necessary to align the connecting elements of the biopsy needle, either manually or through use of a separate spacer, prior to insertion into a biopsy gun. After the biopsy needle is inserted into a biopsy gun, if a spacer clip is used, it is generally necessary to remove the spacer in order to close the lid and operate the biopsy gun. Conventional spacer clips require the molding of a separate spacer. This requirement of a separate molding step adds an additional step in the manufacturing and packaging process thereby increasing the costs to produce the biopsy needle. Moreover, the use of a separate spacer clip may require undue handling of the needle in order to connect and disconnect the spacer clip. Furthermore, some conventional biopsy guns do not permit the option of inserting the needle into a biopsy gun in the uncocked position. By permitting a biopsy needle to be inserted in an uncocked biopsy gun, the proper operation of the needle is checked prior to the gun being fired by moving the inner needle and the outer needle relative to each other during the cocking process. An additional disadvantage of some conventional biopsy needles is that under some conditions, the individual connecting elements slip or rotate relative to the slides they are carried on when inserted in a biopsy gun.

SUMMARY OF THE INVENTION

The present invention includes a biopsy needle particularly suited for use in a biopsy gun. Additionally, the present invention can also be used as a surgical instrument for procedures such as, a microlumpectomy and the removal of microcalcification. The biopsy needle made according to the present invention includes a guiding needle holder that is an integral part of the needle itself that is not removed prior to needle use. The guiding needle holder provides not only an integrated means for grasping and handling the needle, but facilitates needle alignment without the use of extrinsic devices, and prevents rotation and other movement of the needle relative to itself and the slides in a biopsy gun. Additionally, the integrated design of the needle allows the needle to be easily prepackaged in a sterile, disposable condition.

The biopsy needle of the present invention comprises an inner needle with a recess near its beveled distal end, an outer needle displaceably guided on the inner needle and having a beveled distal end, and a guiding needle holder. The gauge and length of the inner needle and outer needle varies with the procedure for which it will be used. The guiding needle holder includes first and second connecting elements, and an integrated spacer. The first connecting element is displaceably guided along the length of the integrated spacer, and the second connecting element is fixedly engaged with the proximal end of the integrated spacer. Both the first and second connecting elements contain a raised annular flange that defines a portion of a bore though the connecting element and assists in maintaining the connecting elements in engagement with the integrated spacer. These bores in the connecting elements allow the needle to be mounted on posts extending from the slides of a biopsy gun. It should be noted that these bores are illustrative of only one way to connect the needle to the slides of a biopsy gun and that other arrangements may be used. The inner needle is embedded in the second connecting element and the outer needle is embedded in the first connecting element. When the first and second connecting elements are maximally displaced relative to each other within the integrated spacer, the distance between the raised annular flange in the first connecting element and the raised annular flange in the second connecting element is such that the biopsy needle can be inserted with the proper spacing into a biopsy gun in the cocked position. This eliminates the need for any external means of achieving the proper spacing of the needle. Alternatively, the needle can be mounted in a biopsy gun in the uncocked position.

Additionally, the present invention can be used to take multiple samples at the same biopsy site as required by procedures such as computer tomography by removing the connecting element carrying the inner needle and replacing it with another connecting element and an inner needle. Once the body is pierced, the biopsy needle is inserted into a biopsy gun and the sample taken. The needle is then removed from the body and the biopsy gun, the sample removed, and the needle can then be reused. All this is accomplished without the use of an external spacer.

In an alternative embodiment, the guiding needle holder incorporates an integrated spacer and a single connecting element. The inner needle is embedded in the integrated spacer and the outer needle is embedded in the connecting element. The biopsy needle can be positioned for insertion into a biopsy gun either in the cocked or uncocked position by maximizing the displacement of the connecting element. In this embodiment, multiple samples can be taken by dislodging the integrated spacer, removing the inner needle and replacing it with another inner needle. The integrated spacer can either be reused or replaced.

It is therefore an advantage of the present invention to provide a biopsy needle that allows a tissue sample to be obtained from a tissue mass which automatically captures and allows the removal of a tissue sample for examination, wherein the inner needle and the outer needle reside and function in an integrated spacer.

It is a further advantage of the present invention to provide an integrated spacer or guiding needle holder that does not require the spacer to be removed prior to operating a biopsy gun.

It is a further advantage of the present invention to provide an integrated spacer that remains inside a biopsy gun during the operation of the gun.

It is a further advantage of the present invention to provide an integrated spacer for a biopsy needle which allows single-handed loading and removal of the needle from a biopsy gun while maintaining the orientation and rotational position of the inner needle and outer needle of a biopsy needle relative to each other and the biopsy gun.

It is a further advantage of the present invention to provide a biopsy needle available in multiple needle gauges and lengths, tailored for various biopsy procedures.

It is a further advantage of the present invention to provide a biopsy needle including an integrated spacer which allows the insertion of the needle into a body, unattached to the biopsy device, without the use of external or removable spacers, and maintains the orientation and proper spacing of the first and second elements to allow the simple insertion of the biopsy needle into a biopsy gun after the needle is inserted into the body, as required by certain biopsy procedures.

It is a further advantage of the present invention to provide a biopsy needle with an integrated spacer that allows the integrated spacer to be gripped by the fingers of the user for manual insertion of the needle into the body while maintaining the special relationship between the inner needle and the outer needle.

It is a further advantage of the present invention to provide a biopsy needle that is prepackaged, sterile and disposable.

It is a further advantage of the present invention to provide a biopsy needle which can be used to obtain multiple biopsy samples from the same biopsy site without the use of an external spacer.

Other features and advantages of the present invention will become readily apparent from the following detailed description, the appended claims and the accompanying drawings. It is to be understood that both the foregoing general description and the following detailed description are exemplary and provided for purposes of explanation only, and are not restrictive of the invention, as claimed.

BRIEF DESCRIPTIONS OF DRAWINGS

DETAILED DESCRIPTION OF THE PREFERRED EMBODIMENT

Figure 1A:
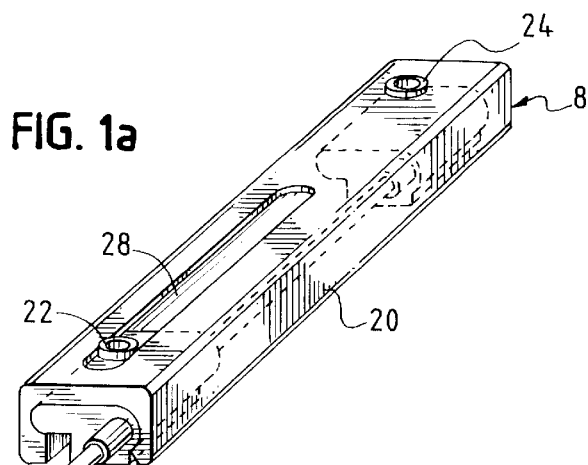
FIG. 1a is an isometric view of one embodiment of the biopsy needle made according to the present invention.
Figure 1B:
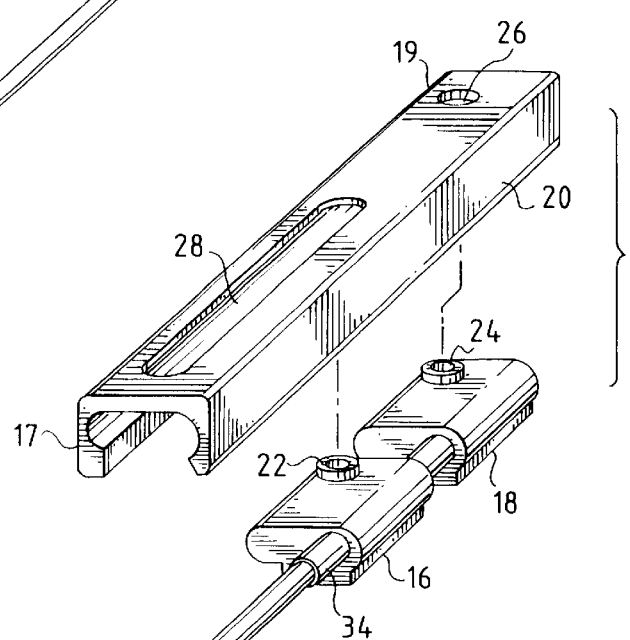
FIG. 1b is an exploded view of the biopsy needle made according to the present invention, positioned so that the recess in the inner needle is exposed.
Figure 1B:
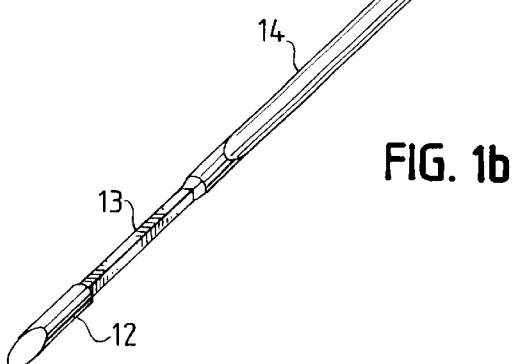

FIGS. 1a and 1b show a preferred embodiment of the biopsy needle 10 made according to the present invention which comprises a guiding needle holder 8, an inner needle 12 and an outer needle 14. The design of the inner needle 12 and the outer needle 14 is generally well known in the art and both have a beveled cutting edge on their distal ends. The inner needle 12 and the outer needle 14 may be of a variety of gauge sizes. The guiding needle holder 8, is used to maintain the relative orientation of the inner needle 12 and the outer needle 14, and to provide a means by which the biopsy needle 10 can be grasped. The guiding needle holder 8 includes an integrated spacer 20, and first and second connecting elements, 16 and 18 respectively.

Figure 2A:
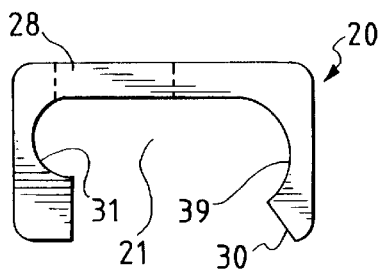
FIG. 2a is an end view of the integrated spacer.

The integrated spacer 20 has an elongated body which includes a slot 28 that extends longitudinally a predetermined distance and a hole 26 that facilitate the insertion of the biopsy needle 10 into a biopsy gun of a type known in the art. As illustrated in FIG. 2a, the integrated spacer 20 has an interior portion 21 that includes a longitudinally extended angled wall 30, a longitudinally extending curved wall 39, and a groove 31, that facilitate the assembly and operation of the biopsy needle 10. The groove 31, angled wall 30, and the curved wall 39, extend longitudinally from the distal end 17 of the integrated spacer 20 through the entire length of the spacer 20. Alternatively, an end wall at the proximal end of the spacer 20 may be provided. The interior portion 21 is configured such that its cross-sectional profile is similar to the cross-sectional profile of the first and second connecting elements 16 and 18 of the needle 10 shown in FIG. 1b.

Figure 2B:
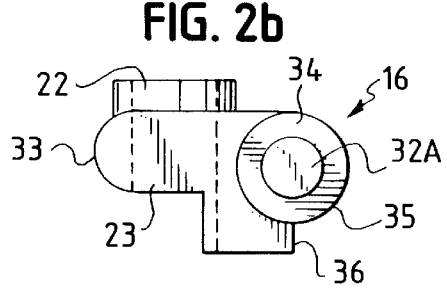
FIG. 2b is an end view of a connecting element.

The first connecting element 16, shown in FIG. 2b, includes a protruding section 33, a sidewall section including a curved portion 35 and a flat portion 36, a longitudinally extending bore 32A that goes through the entire length of the first connecting element 16, and a vertically extending bore 23 which is partially defined by a raised annular flange 22. A portion of the bore 32A is defined by a cylindrical sleeve 34 positioned on one end of the first connecting element 16 shown in FIG. 1b.

For purposes of clarification, when referring to the longitudinally extending bore through second connecting element 18, the longitudinally extending bore will be referred to with reference numeral 32B. The second connecting element 18, illustrated in FIG. 1b, is identical to the first connecting element 16, except that the longitudinally extending bore 32B is not required to extend through the entire length of the second connecting element 18. However, for purposes of ease of manufacture, connecting elements 16 and 18 may be identical. The longitudinally extending bore 32A of the first connecting element 16 holds the proximal end of the outer needle 14 and the longitudinally extending bore 32B of the second connecting element 18 holds the proximal end of the inner needle 12. The connecting elements 16 and 18 are preferably formed by insert molding techniques generally known in the art. The connecting elements 16 and 18 are insert molded around outer needle 14 and inner needle 12, respectively. Although the preferred embodiment illustrates a vertically extending bore 23 in the connecting elements 16 and 18 for engagement to the slides of a biopsy gun, other configurations may be used, such as, for example, flanges.

Figure 3A:
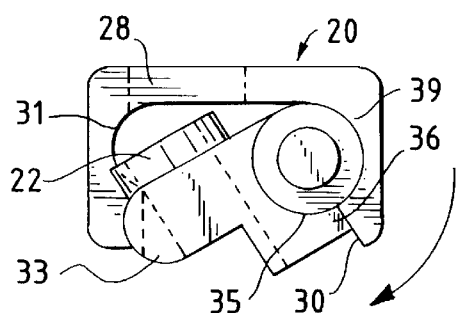
FIG. 3a is an end view demonstrating how the connecting elements are inserted into the integrated spacer to form the guiding needle holder.
Figure 3B:
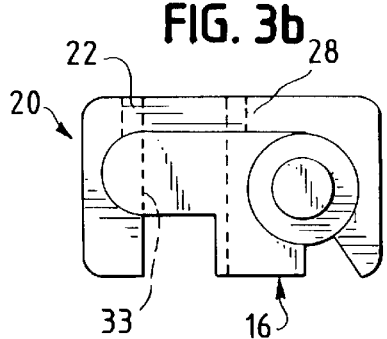
FIG. 3b is an end view of the assembled guiding needle holder.

To assemble the biopsy needle 10, the proximal end portion of the outer needle 14 is fixedly carried in the longitudinally extending bore 32A of the first connecting element 16. The proximal end of the inner needle 12 is removable and fixedly inserted into the longitudinally extending bore 32B of the second connecting element 18. The inner needle 12 is then inserted into the outer needle 14 until the first and second connecting elements 16 and 18 meet. In order to insert the first and second connecting elements 16 and 18 in the integrated spacer 20, both connecting elements 16 and 18 are initially engaged into the integrated spacer 20 with curved portion 35 engaged with the curved wall 39 and flat portion 36 engaged with angled wall 30, as illustrated in FIG. 3a. The second connecting element 18 is rotated into the integrated spacer 20 until the protruding portion 33 snaps into the groove 31 and the second raised annular flange 24 fits into the hole 26 in the integrated spacer 20. The first connecting element 16 is rotated into the integrated spacer 20 until the protruding section 33 snaps into the groove 31 and the first raised annular flange 22 in the first connecting element 16 fits into the slot 28 in the integrated spacer 20, as shown in FIG. 3b. In general use, the biopsy needle 10 remains in this attached configuration throughout its insertion into a biopsy gun and its subsequent use. The length of the longitudinal slot 28 is such that when the outer needle 14 is fully extended, the distance between the first raised annular flange 22 in the first connecting element 16 and the second raised annular flange 24 in the second connecting element 18 is sufficient to enable the flanges to align with the posts on the slides of a biopsy gun when the slides are in the cocked or uncocked positions. The dimensions of the guiding needle holder 8 and the longitudinal slot 28 may be configured to allow the biopsy needle 10 of the present invention to be used in various biopsy guns.

The biopsy needle 10 made according to the present invention provides several advantages over conventional biopsy needles and even those conventional biopsy needles that employ separate spacer clips. For example, when the biopsy needle 10 of the present invention is in its assembled form as illustrated in FIG. 1a, the first connecting element 16 is in the maximally displaced position within the integrated spacer 20. The body of the integrated spacer 20 permits the user to easily grasp the biopsy needle 10 without moving the position of connecting elements 16 and 18 relative to each other. In this position, the distance between the first raised annular flange 22 in the first connecting element 16 and the second raised annular flange 24 in the second connecting element 18 is sufficient to align these holes with posts located on the slides of a cocked biopsy gun, and therefore enable the biopsy needle 10 to be loaded into a biopsy gun without manipulation of the connecting elements 16 and 18. The tip of the inner needle 12 is exposed to facilitate insertion of the biopsy needle 10 into the tissue being sampled.

Figure 5:
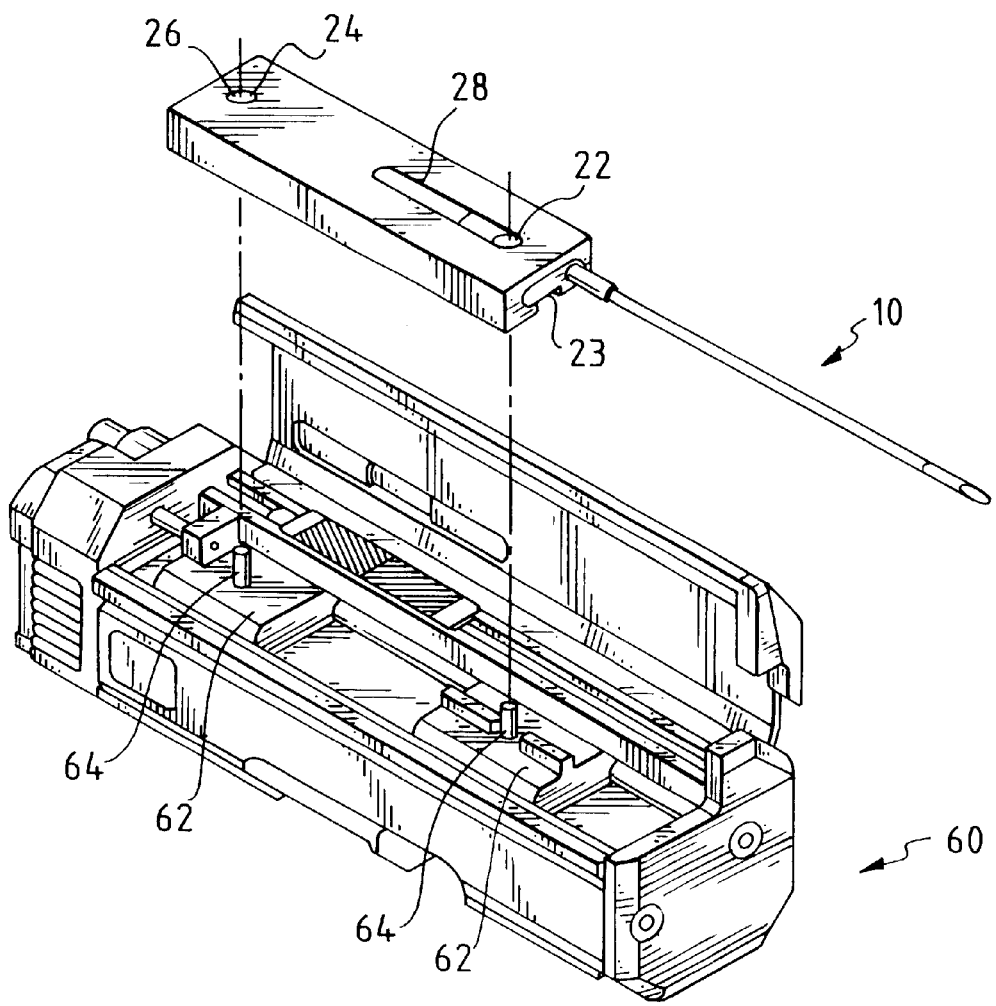
FIG. 5 is an isometric view of one embodiment of the biopsy needle of the present invention used in conjunction with a biopsy gun of a type that is well-known in the art.

The biopsy needle 10 including the integrated spacer 20 can be inserted into a biopsy gun either in the cocked or uncocked position to accommodate the user's preference. The integrated spacer 20 also facilitates removal of the biopsy needle 10 from a biopsy gun without the necessity to reattach a spacer clip as is required with conventional biopsy needles. If the biopsy needle 10 is inserted while the gun is uncocked, the gun should be cocked prior to use. Insertion of the biopsy needle 10 into a biopsy gun 60 is generally straight forward as shown in FIG. 5. The body of the needle holder 8 is grasped by the user and placed over the interior chamber of the biopsy gun 60, as illustrated in FIG. 5. Vertically extending bore 23 of the first and second connecting elements 16 and 18 are aligned over slides 62 of the biopsy gun 60 and receive posts 64. Without having to remove the integrated spacer 20, the lid to the biopsy gun 60 is closed and is ready for use.

The tip of the biopsy needle 10 is inserted into the tissue to be sampled. The biopsy gun is then triggered and the second connecting element 18 along with the integrated spacer 20 is moved forward, while the first connecting element 16 is held stationary. This action is accomplished though the novel arrangement of the guiding needle holder 8 wherein flange 24 of second connecting element 18 engages hole 26 while flange 22 of the first connecting element 16 moves relative to the integrated spacer 20 in slot 28. This movement causes the inner needle 12 to move forward into the tissue being sampled and exposes the recess 13 in the inner needle 12 which receives the tissue to be sampled. The second slide of the biopsy gun is triggered moving the slide engaged with the first connecting element 16 forward. This action causes the outer needle 14 to move forward over the recess 13 which causes the outer needle 14 to separate tissue prolapsed in the recess 13 and secure it therein. The biopsy needle 10, at this point, is back in the position illustrated in FIG. 1a. The biopsy needle 10 can then be removed and the tissue examined. The integrated spacer 20 in engagement with the first and second connecting elements 16 and 18 during operation of the biopsy gun 60, stabilizes the first and second connecting elements 16 and 18 and prevents twisting and bending in the biopsy gun 60.

Multiple samples can be taken at the same biopsy site by either reusing the biopsy needle 10 or replacing the inner needle 12. The inner needle 12 is replaced by removing the second connecting element 18 from the integrated spacer 20, sliding the inner needle 12 out of the outer needle 14, and inserting another inner needle into the outer needle 14 and reattaching the second connecting element 18 in the manner previously described. The second connecting element 18 can either be reused or replaced.

Figure 4A:
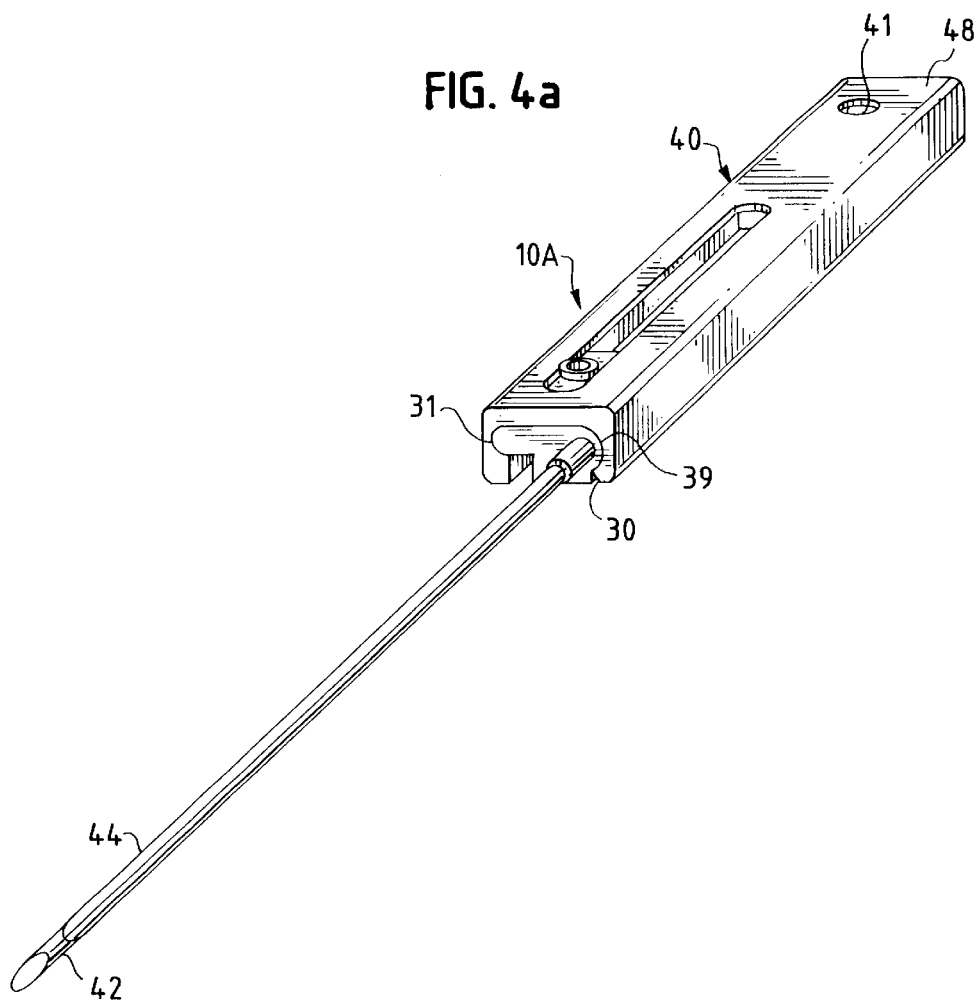
FIG. 4a is an isometric view of an alternative embodiment of the biopsy needle.
Figure 4B:
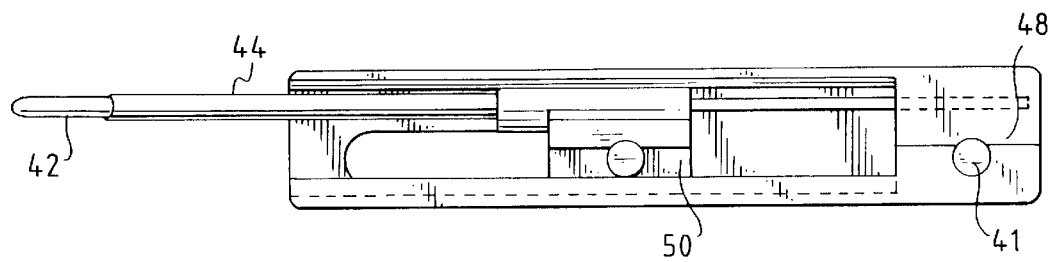
FIG. 4b is the bottom view of an alternative embodiment of the biopsy needle.

An alternative embodiment of the invention is shown in FIGS. 4a and 4b. In this embodiment the biopsy needle 10A includes an inner needle 42, an outer needle 44, and a guiding needle holder 40. The guiding needle holder 40 comprises an integrated spacer 48 and a connecting element 50. Connecting element 50 is identical to connecting element 16 previously described. The integrated spacer is substantially identical to integrated holder 20, except that longitudinally extending groove 31, longitudinally extending wall 30 and longitudinally extending curved wall 39 do not extend as far in the body of the spacer 20. The proximal end of the spacer 48 is solid for ease of manufacturing and includes a vertically extending bore 41. An inner needle 42 is fixedly attached to the integrated spacer 48 near the proximal end, and the outer needle 44 is fixedly attached to the connecting element 50. The connecting element 50 can be attached to the integrated spacer 48 in the manner previously described herewith for attaching the first connecting element 16 in the previous embodiment.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

We claim:

1. A biopsy needle, for use in and removable from a biopsy gun, comprising:
   an inner needle having a first proximal end and a recess in a vicinity of a distal end thereof for receiving a tissue sample;
   an outer needle substantially coaxial with said inner needle having a second proximal end and disposed about a portion of said inner needle;
   an integrated spacer, which includes a slot wherein the slot includes a first closed end and a second closed end, wherein the first closed end and the second closed end define a length there between;
   a first connecting element which includes a first flange displaceably engaged to the slot of the integrated spacer wherein the displacement of the first flange is impeded by the first closed end and the second closed end and the first connecting element is connected to said proximal end of said outer needle; and
   a second connecting element which includes a second flange fixedly engaged to the integrated spacer and said second connecting element is fixedly connected to said inner needle such that said second connecting element does not move relative to said integrated spacer.

2. A biopsy needle as claimed in claim 1, wherein said first connecting element is displaceably guided along the length of the slot of said integrated spacer, wherein the length defines a distance sufficient to enable operation of said biopsy needle in a biopsy gun.

3. A biopsy needle as claimed in claim 2, wherein the integrated spacer includes a hole and an initial distance defined by the second closed end and the hole, wherein the initial distance enables insertion of said biopsy needle in a biopsy gun when the first connecting element is positioned at the second closed end.

4. A biopsy needle as claimed in claim 3, wherein
   said integrated spacer having an interior section including a longitudinally extending groove, a curved wall, and an angled wall;
   said first connecting element includes a first protruding section engaged to the groove of said integrated spacer, a first curved position that fits in the curved wall of said integrated spacer; and
   said second connecting element includes a second protruding section engaged to the groove of said integrated spacer, and a second curved portion engaged to the curved wall of said integrated spacer.

5. A biopsy needle as claimed in claim 4, wherein the connecting element is displaceably guided along the length of the slot of said integrated spacer wherein the length equals a distance sufficient to enable insertion of said biopsy needle into a biopsy gun.

6. A needle holder for guiding a biopsy needle set for use in and removable from a biopsy gun comprising:
   an integrated spacer which includes a hole and a slot wherein the slot includes a first closed end proximal to the hole and a second closed end distal from the hole, wherein the first closed end and the second closed end define a length there between;
   a first connecting element which includes a first flange connected in the slot of the integrated spacer such that it is displaceable relative to said integrated spacer and such displacement is impeded by the first closed end and the second closed end; and
   a second connecting element which includes a second flange fixedly connected to the first hole in said integrated spacer.

7. A biopsy needle as claimed in claim 6, wherein
   said integrated spacer includes a longitudinally extending groove, a curved wall, and an angled wall; and
   said connecting elements includes a protruding section engaged to the groove of said integrated spacer, a curved portion that fits in the curved wall of said integrated spacer, and a flat portion.

8. A needle holder for guiding a biopsy needle set for use in and removable from a biopsy gun comprising:
   an integrated spacer which includes a first hole and a slot wherein the slot includes a first closed end proximal to the first hole and a second closed end distal from the first hole, wherein the first closed end and the second closed end define a length there between; and
   a connecting element which includes a raised hole displaceably connected in the slot in said integrated spacer.

9. A guiding needle holder as claimed in claim 8, wherein said connecting element is displaceably guided along the length of the slot of said integrated spacer, wherein the length defines a distance sufficient to enable insertion of a biopsy needle into a biopsy gun.

10. A guiding needle holder as claimed in claim 9, wherein
    said integrated spacer includes a longitudinally extending groove, a curved wall, and an angled wall;
    said first connecting element includes a first protruding section that fits in the groove of said integrated spacer, a first curved portion that fits in the curved wall of said integrated spacer, a first portion, and a first longitudinal bore; and
    said second connecting element includes a second protruding section that fits in the groove of said integrated spacer, a second curved portion that fits in the curved wall of said integrated spacer, a second flat portion and a second longitudinal bore.

11. A biopsy instrument for use in and removable from a biopsy gun comprising:
    a hollow outer needle;
    an inner needle extending through said hollow outer needle, wherein said inner needle includes a recess near the distal end thereof, said inner needle and said outer needle movable relative to each other permitting selective encapsulation of said recess on said inner needle by said outer needle;
    a connecting element attached to a proximal end of said outer needle; and
    an integrated spacer attached to a proximal end of said inner needle, said connecting element engaged to said integrated spacer for relative movement therein whereby said inner needle is selectively moved between positions exposing the recess of said inner needle and encapsulating the recess of said inner needle when said biopsy instrument is contained within a biopsy gun.

12. A needle holder for holding an inner needle and a hollow outer needle, wherein the inner needle comprises a recess near the distal end thereof and extends through the hollow outer needle and the outer and inner needles are movable relative to each other, comprising:
    a connecting element attached to a proximal end of the outer needle; and
    an integrated spacer attached to a proximal end of the inner needle, the connecting element engaged to said integrated spacer for relative movement therein whereby the inner needle is selectively moved to a position exposing the recess of the inner needle and the outer needle is moved to a position encapsulating the recess of said inner needle when said needle holder is contained within a biopsy gun, wherein the inner needle is operatively fixed to said integrated spacer when the inner needle and outer needle are moved to expose and encapsulate the recess and wherein said needle holder is removable from the biopsy gun and wherein said connecting element remains engaged to said integrated spacer and the inner needle remains operatively fixed to said integrated spacer when the biopsy instrument is removed from the biopsy gun.

13. A guiding needle holder as claimed in claim 12, wherein,
said integrated spacer includes a longitudinally extending groove, a curved wall, an angled wall, and a first longitudinal bore; and
said connecting element includes a protruding section that fits in the groove of said integrated spacer, a curved portion that fits in the curved wall of said integrated spacer, a flat portion, and a second longitudinal bore.

14. A needle bolder as claimed in claim 13, wherein said integrated spacer further comprises:
a hole and a slot;
said connecting element further comprises a first flange displaceably engaged to the slot of said integrated spacer; and
said second connecting element includes a second flange fixedly engaged to the hole of said integrated spacer.

15. A needle holder as claimed in claim 14, wherein said connecting element is displaceably guided along the length of the slot of said integrated spacer a distance sufficient to enable operation of said biopsy needle in a biopsy gun.

16. A needle holder as claimed in claim 15, wherein said connecting element is positioned along the length of the slot of said integrated spacer a predetermined distance to enable insertion of said biopsy needle in a biopsy gun.

17. A needle holder for holding an inner needle and a hollow outer needle, wherein the inner needle comprises a first proximal end, a distal end and a recess near the distal end thereof and extends through the hollow outer needle and the outer and inner needles are movable relative to each other, comprising:
an integrated spacer which includes a slot wherein the integrated spacer is operatively fixed to the first proximal end when the inner needle and outer needle are moved relative to each other and wherein the slot includes a first closed end and a second closed end, wherein the first closed end and the second closed end define a length there between; and
a first connecting element coupled to a proximal end of the outer needle, said first connecting element displaceably and directly connected to said integrated spacer allowing the outer needle and said first connecting element to move longitudinally along the length relative to said integrated spacer.

18. The needle holder as claimed in claim 17 further comprising a second connecting element coupled to a proximal end of the inner needle, said second connecting element fixably connected to said integrated spacer.

19. The needle holder as claimed in claim 18, wherein said integrated spacer comprises:
a hole and a slot;
said first connecting element includes a first flange displaceably engaged to the slot of said integrated spacer; and
said second connecting element includes a second flange fixedly engaged to the hole of said integrated spacer.

20. A The needle holder as claimed in claim 19, wherein said first connecting element is displaceably guided along the length of the slot of said integrated spacer a distance sufficient to enable operation of said needle holder in a biopsy gun.

21. A needle holder as c;ao,ed om c;ao, 20, wherein
said integrated spacer has an interior section comprising a longitudinally extending groove, a curved wall, and an angled wall;
said connecting element further comprises a first protruding section engaged to the groove of said integrated spacer, a first curved portion that fits in the curved wall of said integrated spacer; and
said second connecting element further comprises a second protruding section engaged to the groove of said integrated spacer, and a second curved portion engaged to the curved wall of said integrated spacer.

22. A biopsy needle for use in and removable from a biopsy gun comprising:
an integrated spacer which includes a hole and a slot;
an inner needle having a recess in a vicinity of a distal end thereof for receiving a tissue sample, and a proximal end in a fixed position relative to said integrated spacer;
an outer needle substantially coaxial with said inner needle and disposed about a portion of said inner needle having a proximal end, such that said inner needle is moved relative to said outer needle to expose the recess and said outer needle is moved away from said proximal of said inner needle to enable said outer needle to encapsulate the recess;
wherein said inner needle is operatively fixed to said integrated spacer when said inner needle and outer needle are moved to expose and encapsulate the recess;
a first connecting element coupled to said proximal end of said outer needle, said first connecting element displaceably and directly connected to said integrated spacer allowing said outer needle and said first connecting element to move longitudinally relative to said integrated spacer, said first connecting element including a first flange displaceably engaged to the slot of the integrated spacer; and
a second connecting element coupled to said proximal end of said inner needle and including a second flange fixedly engaged to the hole of said integrated spacer.

23. A biopsy needle for use in and removable from a biopsy gun comprising:
an integrated spacer which includes a slot;
an inner needle having a recess in a vicinity of a distal end thereof for receiving a tissue sample, and a proximal end in a fixed position relative to said integrated spacer;
an outer needle substantially coaxial with said inner needle and disposed about a portion of said inner needle having a proximal end, such that said inner needle is moved relative to said outer needle to expose the recess and said outer needle is moved away from said proximal of said inner needle to enable said outer needle to encapsulate the recess;
wherein said inner needle is fixed to said integrated spacer when said inner needle and outer needle are moved to expose and encapsulate the recess; and
a connecting element coupled to said proximal end of said outer needle, said connecting element displaceably and directly connected to said integrated spacer allowing said outer needle and said connecting element to move longitudinally relative to said integrated spacer said connecting element including a flange displaceably engaged to the slot of the integrated spacer.

24. The needle holder as claimed in claim 23, wherein said integrated spacer comprises:

a hole and a slot;

said first connecting element includes a first flange displaceably engaged to the slot of said integrated spacer; and said second connecting element includes a second flange fixedly engaged to the hole of said integrated spacer.

25. The needle holder as claimed in claim 24, wherein said first connecting element is displaceably guided along the length of the slot of said integrated spacer a distance sufficient to enable operation of said needle holder in a biopsy gun.

26. The needle holder as claimed in claim 25, wherein said first connecting element is positioned along the length of the slot of said integral spacer a predetermined distance to enable insertion of said needle holder in a biopsy gun.

27. The needle holder as claimed in claim 23, wherein:

said integrated spacer further comprises an interior section including a longitudinally extending groove, a curved wall, and an angled wall;

said first connecting element further comprises a first protruding section engaged to the groove of said integrated spacer, a first curved portion that fits in the curved wall of said integrated spacer; and said second connecting element further comprises a second protruding section engaged to the groove of said integrated spacer, and a second curved portion engaged to the curved wall of said integrated spacer.

28. A biopsy needle for use in and removable from a biopsy gun comprising:

an integrated spacer which includes a hole and a slot;

an inner having a recess in a vicinity of a distal end thereof for receiving a tissue sample, and a proximal end in a fixed position relative to said integrated spacer;

an outer needle substantially coaxial with said inner needle and disposed about a portion of said inner needle having a proximal end, such that said inner needle is moved relative to said outer needle to expose the recess and said outer needle is moved away from said proximal of said inner needle to enable said outer needle to encapsulate the recess;

wherein said inner needle is operatively fixed to said integrated spacer when said inner needle and outer needle are moved to expose and encapsulate the recess;

a first connecting element coupled to said proximal end of said outer needle, said first connecting element displaceably and directly connected to said integrated spacer allowing said outer needle and said first connecting element to move longitudinally relative to said integrated spacer, said first connecting element including a first flange displaceably engaged to the slot of the integrated spacer; and a second connecting element coupled to said proximal end of said inner needle and including a second flange fixedly engaged to the hole of said integrated spacer.

29. A biopsy needle for use in and removable from a biopsy gun comprising:

an integrated spacer which includes a slot;

an inner need having a recess in a vicinity of a distal end thereof for receiving a tissue sample, and a proximal end in a fixed position relative to said integrated spacer;

an outer needle substantially coaxial with said inner needle and disposed about a portion of said inner needle having a proximal end, such that said inner needle is moved relative to said outer needle to expose the recess and said outer needle is moved away from said proximal of said inner needle to enable said outer needle to encapsulate the recess;

wherein said inner needle is fixed to said integrated spacer when said inner needle and outer needle are moved to expose and encapsulate the recess; and a connecting element coupled to said proximal end of said outer needle, said connecting element displaceably and directly connected to said integral spacer allowing said outer needle and said connecting element to move longitudinally relative to said integrated spacer said connecting element including a flange displaceably engaged to the slot of the integrated spacer.

* * * * *